United States Patent [19]

Ikeda et al.

[11] Patent Number: 4,814,460
[45] Date of Patent: * Mar. 21, 1989

[54] PROCESS FOR PREPARING E-ISOMER OF TRIAZOLYL STYRYL KETONE DERIVATIVE

[75] Inventors: Takaharu Ikeda, Toyonaka; Kazuhiro Tada, Kyoto; Haruki Morino, Toyonaka, all of Japan

[73] Assignee: Sumitomo Chemical Company, Limited, Osaka, Japan

[*] Notice: The portion of the term of this patent subsequent to Mar. 21, 2006 has been disclaimed.

[21] Appl. No.: 30,233

[22] Filed: Mar. 26, 1987

[30] Foreign Application Priority Data

Mar. 28, 1986 [JP] Japan ................. 61-071988

[51] Int. Cl.$^4$ .......................... C07D 249/12
[52] U.S. Cl. ........................ 548/262; 568/310
[58] Field of Search ............... 548/262; 568/384, 310, 568/341

[56] References Cited

U.S. PATENT DOCUMENTS 4,018,718 4/1977 Ochsner et al. ............ 568/339

FOREIGN PATENT DOCUMENTS

| 57-102872 | 6/1982 | Japan | 548/262 |
| 58-140081 | 8/1983 | Japan | 548/262 |
| 58-140082 | 8/1983 | Japan | 548/262 |
| 58-146575 | 8/1983 | Japan | 548/262 |
| 58-174373 | 10/1983 | Japan | 548/262 |

OTHER PUBLICATIONS

Baranyai et al., "Determination of the Geometric, etc.", CA 95: 169538d (1981).
Cobb et al., "Isomerization of Cis, Trans, etc.", CA 97: 200936t (1977).

Primary Examiner—Glennon H. Hollrah
Assistant Examiner—Patricia L. Morris
Attorney, Agent, or Firm—Birch, Stewart, Kolasch & Birch

[57] ABSTRACT

A novel process for preparing the E-isomer of triazolyl styryl ketone derivative of the formula (I):

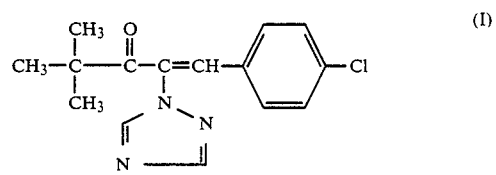

is disclosed. The process includes treating the Z-isomer of the derivative which may contain the E-isomer of the derivative with an acid and an isomerization catalyst in an organic solvent, precipitating and separating the resulting salt of E-isomer from the solution, and decomposing the resulting precipitate to obtain the E-isomer of the derivative free from the acid. The E-isomer is useful for preparing the E-isomer of triazolyl styryl carbinol of the formula (II):

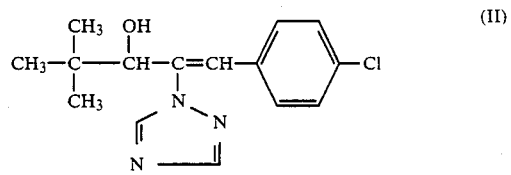

which is useful as an antimicrobial agent, a herbicide, a plant growth regulator, or the like.

15 Claims, No Drawings

PROCESS FOR PREPARING E-ISOMER OF TRIAZOLYL STYRYL KETONE DERIVATIVE

The present invention relates to a novel process for preparing the E-isomer of 1-(4-chlorophenyl)-2-(1,2,4-triazol-1-yl)-4,4-dimethyl-1-penten-3-one (hereinafter referred to as "triazolyl styryl ketone derivative") of the formula (I):

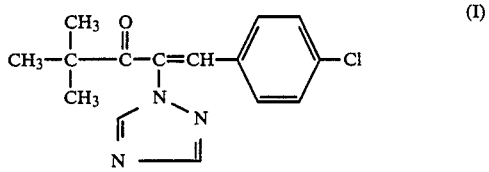

BACKGROUND OF THE INVENTION

It is known that the triazolyl styryl ketone derivative (I) itself is usful as an antimicrobial agent [cf. Japanese Patent First Publication (Kokai) No. 130661/1978], and that triazolyl styryl carbinol of the formula (II):

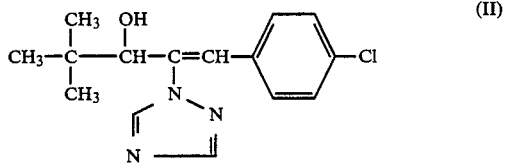

which is obtained by reduction of the above derivative (I) is more useful as an antimicrobial agent, a herbicide, a plant growth regulator, or the like, and it is also known that the effect of the E-isomer thereof is particularly superior to that of the Z-isomer [cf. Japanese Patent First Publication (Kokai) No. 41875/1979, 124771/1980 and 25105/1981].

Accordingly, it is desirable to provide a process for efficiently preparing the E-isomer of the triazolykl styryl ketone derivative of the above formula (I) which is a starting material for preparing the E-isomer of the above compound of the formula (II) h(hereinafter the E-isomer, the Z-isomer and a mixture of the E-isomer and the Z-isomer of the triazolyl styryl ketone derivative (I) are simply refered to as "E-isomer", "Z-isomer" and "E/Z-isomer", respectively, unless specified otherwise). As a process for satisfying such requirements, for example, the following processes are proposed:

(1) A process of isomerizing Z-isomer or E/Z-isomer into E-isomer with light [cf. Japanese Patent First Publication (Kokai) No. 147265/1980].

(2) A process of isomerizing Z-isomer or E/Z-isomer with a compound such as an aromatic mercaptan [cf. Japanese Patent First Publication (Kokai) No. 147265/1980].

(3) A process of separating E/Z-isomer with a chromatography [cf. Jpanese Patent First Publication (Kokai) No. 147265/1980].

(4) A process of separating E-isomer from E/Z-isomer, which comprises treating E/Z-isomer with sulfuric acid, precipitating and separating the sulfuric acid salt of E-isomer, and decomposing the salt to obtain E-isomer [cf. Japanese Patent First Publication (Kokai) No. 140081/1983].

However, these processes have problems such as, for example, the mecessity of a special reaction apparatus or the necessity of an additional treatment for separating E- and Z-isomers from the reaction products because of an insufficient isomerizatio rate. Moreover, in the case of the process for merely separating E-isomer from E/Z-isomer such as the process (4), the yield of the E-isomer is dependent on the E-isomer content contained in the starting E/Z-isomer and the treatment of the residual Z-isomer is also necessary.

BRIEF DESCRIPTION OF THE INVENTION

In view of the above circumstances, the present inventors have extensively investigated a process which is free from the above problems and can produce easily and effectively the desired E-isomer from Z-isomer or E/Z-isomer on an industrial scale and in a good yield, and have found a process which can perform simultaneously the isomerization of Z-isomer or E/Z-isomer and the separation of E-isomer and can satisfy the above-mentioned requirements.

Thus, the object of the present invention is to provide a novel process for preparing the E-isomer of the triazolyl styryl ketone derivative of the above formula (I), which comprises treating the Z-isomer of the derivative which may contain the E-isomer with an acid and an isomerization catalyst in an organic solvent, precipitating and separating the resulting salt of the E-isomer from the solution, and decomposing the precipitate to obtain the E-isomer of the derivative free from the acid.

DETAILED DESCRIPTION OF THE INVENTION

The starting material used in the present invention may be either Z-isomer or E/Z-isomer, i.e. a mixture of E-isomer and Z-isomer wherein the E-isomer content is not limited.

The acid used in the present invention includes sulfuric acid, sulfonic acids (e.g. methanesulfonic acid, ethanesulfonic acid, etc.), hydrohalogenic acids (hydrochloric acid, hydrobromic acid, etc.), nitric acid, chloric acid, perchloric acid, aliphatic carboxylic acids (e.g. acetic acid, propionic acid, etc.) and the like. Among these acids, the preferable ones are sulfuric acid or methanesulfonic acid. Although the amount of the acid varies depending on the kind of acid, it is usually used in an amount of 0.5 to 3 moles, preferably 0.8 to 1.2 moles, per 1 mole of the starting Z-isomer or E/Z-isomer. An appropriate amount of water may optionally be added when the acid is used.

The isomerization catalyst used in the present invention is not limited and may be any isomerization catalysts which have an ability to isomerize Z-isomer into E-isomer in the presence of an acid. The preferable isomerization catalyst includes compounds which can form a halonium ion, and includes, for example, halogens (e.g. chlorine, bromine, iodine, etc.), halohalides (e.g. iodine monobromide, etc.), cyanogen halides (e.g. cyanogen bromide, etc.) N-halocarboxylic amides or N-halodicarboxylic imides (e.g. N-bromosuccinimide, N-bromoacetamide, N-bromocaprolactam, N-bromophthalimide, etc.), hypohalogenous acids (e.g. trifluoroacetyl hypobromite, etc.), complexes of a halogen with an organic compound (e.g. triphenylphosphine dibromide, etc.), and the like. The isomerization catalyst is usually used in an amount of 0.0001 to 1.0 mole, preferably 0.001 to 0.1 mole, per 1 mole of the starting Z-isomer or Z-isomer contained in E/Z-isomer.

The solvent used in the present invention is not limited and includes, preferably, aprotic organic solvents, for example, aromatic hydrocarbons (e.g. benzene, xylene, toluene, etc.), halogenated hydrocarbons (e.g. dichloromethane, chloroform, carbon tetrachloride, dichloroethane, trichlene, perchlene, monochlorobenzene, dichlorobenzene, etc.), esters (e.g. ethyl acetate, ethyl formate, etc.), ethers (e.g. diethyl ether, tetrahydrofuran, etc.), aliphatic or alicyclic hydrocarbons (e.g. hexane, heptane, octane, petroleum ether, cyclohexane, etc.), and a mixture thereof. Although the amount of the solvent varies largely depending on, for example, the kind of the solvent, the kind of the isomerization catalyst, and the like, it is usually used in an amount of 0.5 to 20-fold by weight of the starting Z-isomer or E/Z-isomer.

The reaction is usually carried out at a temperature of from 0° to 20° C., preferably from 30° to 150° C., for 0.5 to 48 hours.

The isomerization of Z-isomer into E-isomer proceeds by treating Z-isomer or E/Z-isomer with an acid and an isomerization catalyst, by which a salt of E-isomer is produced. After the reaction, the reaction mixture is cooled to precipitate the salt of E-isomer from the mixture. In general, the salt of E-isomer precipitates spontaneously, as a crystal, from the reaction mixture with the progress of the reaction, or by cooling the reaction mixture, while a seed crystal may be used to ensure the precipitation of the salt.

The separation of the precipitated salt of E-isomer from the reaction mixture is carried out by a conventional method such as filtration, centrifugation, decantation, or the like.

The recovery of E-isomer from the salt of E-isomer is carried out by salt-decomposition or neutralization of the resulting salt. For example, the salt of E-isomer can be decomposed by mixing the salt with an excess of water and a solvent which is immiscible with water and can dissolve E-isomer (e.g. toluene, monochlorobenzene, etc.), to obtain a high purity of E-isomer from the organic layer. The decomposition of the salt of E-isomer may also be carried out by using a protic solvent except water (e.g. methanol, acetic acid, etc.). Alternatively, E-isomer can be obtained by neutralizing the salt thereof with an aqueous solution of a base such as sodium hydroxide, sodium bicarbonate, sodium carbonate, or the like.

According to the present invention, Z-isomer can easily be isomerized into E-isomer in a good yield on an industrial scale, without using a special apparatus. Moreover, a high purity of E-isomer which does not contain any substantial amount of by-product can be obtained.

The present invention is illustrated by the following Examples, but should not be construed to be limited thereto. In the Examples, "%" and "ratio" mean "% by weight" and "ratio by weight", respectively, unless specified otherwise.

EXAMPLE 1

Z-isomer of 1-(4-chlorophenyl)-2-(1,2,4-triazol-1-yl)-4,4-dimethyl-1-penten-3-one (2.5 g) was dissolved in carbon tetrachloride (10 g), and thereto were added dropwise conc. sulfuric acid (0.845 g; sulfuric acid content: 97%) and then bromine (0.041 g) at 20° C. After reacting the mixture at a temperature of from 40° C. to 50° C. for 20 days, the mixture was cooled to 20° C., and the resulting crystals were separated by filtration. The crystals were washed with chloroform (10 g), and thereto were added 10% aqueous sodium bicarbonate (2 g), chloroform (20 g) and water (10 g). After stirring the mixture at room temperature until the crystals disappeared, the aqueous layer was removed from the mixture, and the chloroform layer was washed twice with water and then concentrated to obtain E-isomer of 1-(4-chlorophenyl)-2-(1,2,4-triazol-1-yl)-4,4-dimethyl-1-penten-3-one. The yield of E-isomer to the starting Z-isomer was 79.8%, and the ratio of E-isomer to Z-isomer (hereinafter referred to as "E/Z ratio", unless specified otherwise) was 98.6/1.4.

EXAMPLES 2 AND 3

Using the same kind and amount of Z-isomer as used in Example 1, Example 1 was repeated to obtain E-isomer, except that a different kind of solvent and an amount thereof, a reaction temperature and a reaction time as shown in Table 1 were employed. The results are shown in Table 1.

TABLE 1

| | Solvent | | Reaction temperature (°C.) | Reaction time (days) | Yield of E-isomer (%) | E/Z ratio (by weight) |
|---|---|---|---|---|---|---|
| | Kind | Amount (g) | | | | |
| Ex. 2 | 1,2-Dichloroethane | 10 | 20–25 | 14 | 51.6 | 95.8/4.2 |
| | n-Heptane | 10 | | | | |
| Ex. 3 | Chloroform | 10 | 40–45 | 4 | 69.5 | 99.4/0.6 |
| | n-Heptane | 10 | | | | |

EXAMPLE 4

A crude mixture of E-isomer and Z-isomer of 1-(4-chlorophenyl)-2-(1,2,4-triazol-1-yl)-4,4-dimethyl-1-penten-3-one (5.0 g; E/Z ratio: 21.2/78.8) was dissolved in monochlorobenzene (20 g), and thereto were added dropwise conc. sulfuric acid (1.69 g; sulfuric acid content: 97%) and then bromine (0.082 g) at 20° C. After reacting the mixture at a temperature of from 40° to 45° C. for 4 days, the mixture was cooled to 20° C., and the resulting crystals were separated by filtration. The crystals were washed with chloroform (20 g), and thereto were then added 10% aqueous sodium bicarbonate (4 g), water (20 g) and chloroform (40 g), and the mixture was stirred at room temperature until the crystals disappeared. The aqueous layer was then removed from the mixture, and the chloroform layer was washed twice with water and concentrated to obtain E-isomer of 1-(4-chlorophenyl)-2-(1,2,4-triazol-1-yl)-4,4-dimethyl-1-penten-3-one. The yield of E-isomer to the starting E/Z-isomer was 51.6%, and the E/Z ratio was 97.4/2.6.

EXAMPLE 5

An E-isomer/Z-isomer mixture of 1-(4-chlorophenyl)-2-(1,2,4-traizol-1-yl)-4,4-dimethyl-1-penten-3-one (28.98 g; E/Z ratio: 30.5/69.5) was dissolved in monochlorobenzene (115.92 g), and thereto were added dropwise methanesulfonic acid (9.61 g) and then bromine (0.48 g) at 30° C. After reacting the mixture at 40° C. for 30 hours, the mixture was cooled to 25° C., and the resulting crystals were separated by filtration. The crystals were washed with monochlorobenzene (60 g), and thereto were added water (20 g) and monochlorobenzene (150 g), and the mixture was stirred at 60° C. until the crystals disappeared. The aqueous layer was then removed from the mixture, and the monochlorobenzene layer was washed with 5% aqueous sodium bicarbonate and water, and concentrated to obtain E-isomer of 1-(4-chlorophenyl)-2-(1,2,4-triazol-1-yl)-4,4-dimethyl-1-penten-3-one. The yield of E-isomer to the starting E/Z-isomer was 92.1%, and the E/Z ratio was 99.8/0.2.

EXAMPLE 6

A mixture of E-isomer and Z-isomer of 1-(4-chlorophenyl)-2-(1,2,4-triazol-1-yl)-4,4-dimethyl-1-penten-3-one (14.49 g; E/Z ratio: 30.5/69.5) was dissolved in monochlorobenzene (57.95 g), and thereto were added dropwise methanesulfonic acid (4.81 g) and then N-bromosuccinimide (0.44 g) at 30° C. After reacting the mixture at 80° C. for 2 hours, the mixture was cooled to 25° C. over about 4 hours, and the resulting crystals were separated by filtration. The crystals were washed with monochlorobenzene (30 g), and thereto were added water (10 g) and monochlorobenzene (75 g), and the mixture was stirred at 60° C. until the crystals disappeared. The aqueous layer was removed from the mixture, and the monochlorobenzene layer was washed with 5% aqueous sodium bicarbonate and water, and concentrated to obtain E-isomer of 1-(4-chlorophenyl)-2-(1,2,4-triazol-1-yl)-4,4-dimethyl-1-penten-3-one. The yield of E-isomer to the starting E/Z-isomer was 95.9%, and the E/Z ratio was 99.0/1.0.

We claim:

1. A process for preparing the E-isomer of the triazolyl styryl ketone derivative of the formula (I):

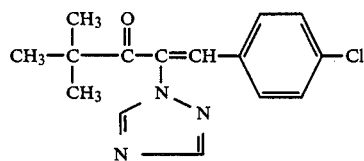

(I)

which comprises treating the Z-isomer of said derivative which may contain the E-isomer of said derivative with an acid and an isomerization catalyst, which is capable of releasing a halonium ion, in an organic solvent, precipitating and separating the resulting salt of the E-isomer from the solution, and decomposing the resulting precipitate to obtain the E-isomer of said derivative free from acid.

2. The process according to claim 1, wherein the acid is a member selected from the group consisting of sulfuric acid, a sulfonic acid, a hydrohalogenic acid, acetic acid, and propionic acid.

3. The process according to claim 2, wherein the acid is sulfuric acid or methanesulfonic acid.

4. The process according to claim 1, wherein the acid is used in an amount of 0.5 to 3 moles per 1 mole of the starting Z-isomer or E/Z-isomer.

5. The process according to claim 1, wherein the halonium ion is bromonium ion.

6. The process according to claim 1, wherein the isomerization catalyst is a member selected from the group consisting of a halogen, iodine monobromide, a cyanogen halide, N-bromosuccinimide, N-bromoacetamide, N-bromocaprolactam, N-bromophthalimide, trifluoroacetyl hypobromite, and triphenylphosphine dibromide.

7. The process according to claim 1, wherein the isomerization catalyst is used in an amount of 0.0001 to 1.0 mole per 1 mole of the starting Z-isomer or the Z-isomer contained in E/Z-isomer.

8. The process according to claim 1, wherein the reaction is carried out at a temperature of from 30° C. to 150° C.

9. The process according to claim 1, wherein the precipitated and separated salt of the E-isomer is decomposed by mixing said salt with a mixture of water and a solvent which is immiscible with water and can dissolve the E-isomer.

10. The process according to claim 9, wherein the salt of the E-isomer is neutralized and decomposed by further adding an alkali.

11. The process according to claim 1, wherein the acid is a member selected from the group consisting of nitric acid, chloric acid, and perchloric acid.

12. The process according to claim 2, wherein said hydrohalogenic acid is a member selected from the group consisting of hydrochloric acid and hydrobromic acid.

13. The process according to claim 1, wherein the solvent is a member selected from the group consisting of benzene, xylene, toluene, dichloromethane, chloroform, carbon tetrachloride, dichloroethane, trichlene, perchlene, monochlorobenzene, dichlorobenzene, ethyl acetate, ethyl formate, diethyl ether, tetrahydrofuran, hexane, heptane, octane, petroleum ether, cyclohexane, and mixtures thereof.

14. The process according to claim 1, wherein the solvent is used in an amount of 0.5 to 20-fold by weight of the starting Z-isomer or E/Z-isomer.

15. The process according to claim 1, wherein the reaction is conducted for 0.5 to 48 hours.

* * * * *